(12) United States Patent
Arno

(10) Patent No.: US 7,723,685 B2
(45) Date of Patent: *May 25, 2010

(54) MONITORING SYSTEM COMPRISING INFRARED THERMOPILE DETECTOR

(75) Inventor: Jose I. Arno, Brookfield, CT (US)

(73) Assignee: Advanced Technology Materials, Inc., Danbury, CT (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/060,686

(22) Filed: Apr. 1, 2008

(65) Prior Publication Data

US 2009/0039266 A1 Feb. 12, 2009

Related U.S. Application Data

(60) Continuation of application No. 11/555,094, filed on Oct. 31, 2006, now Pat. No. 7,351,976, which is a continuation of application No. 10/668,489, filed on Sep. 23, 2003, now Pat. No. 7,129,519, which is a continuation-in-part of application No. 10/623,244, filed on Jul. 18, 2003, now Pat. No. 7,011,614, which is a division of application No. 10/140,848, filed on May 8, 2002, now Pat. No. 6,617,175.

(51) Int. Cl.
*G01J 5/02* (2006.01)
(52) U.S. Cl. .................................................. 250/343
(58) Field of Classification Search .................. 250/343
See application file for complete search history.

(56) References Cited

U.S. PATENT DOCUMENTS

| | | | |
|---|---|---|---|
| 4,647,777 A | 3/1987 | Meyer | |
| 4,816,294 A | 3/1989 | Tsuo et al. | |
| 4,859,859 A * | 8/1989 | Knodle et al. | 250/504 R |
| 4,935,345 A | 6/1990 | Guilbeau et al. | |
| 5,047,352 A | 9/1991 | Stetter et al. | |
| 5,262,645 A * | 11/1993 | Lambert et al. | 250/339.04 |
| 5,282,473 A | 2/1994 | Braig et al. | |
| 5,367,167 A | 11/1994 | Keenan | |
| 5,404,125 A | 4/1995 | Mori et al. | |
| 5,464,983 A | 11/1995 | Wang | |

(Continued)

OTHER PUBLICATIONS

Adrian, Peter, "Sensor industry developments and trends", "Sensor Business Digest", Oct. 2001, Publisher: Vital Information Publication.

(Continued)

*Primary Examiner*—David P Porta
*Assistant Examiner*—Mindy Vu
(74) *Attorney, Agent, or Firm*—Steven J. Hultguist; Intellectual Proper Technology Law; Chih-Sheng Lin

(57) ABSTRACT

The present invention relates to a semiconductor processing system that employs infrared-based thermopile detector for process control, by analyzing a material of interest, based on absorption of infrared light at a characteristic wavelength by such material. In one embodiment, an infrared light beam is transmitted through a linear transmission path from an infrared light source through a sampling region containing material of interest into the thermopile detector. The linear transmission path reduces the risk of signal loss during transmission of the infrared light. The transmission path of the infrared light may comprise a highly smooth and reflective inner surface for minimizing such signal loss during transmission.

20 Claims, 8 Drawing Sheets

U.S. PATENT DOCUMENTS

| | | | |
|---|---|---|---|
| 5,589,689 A | 12/1996 | Koskinen | |
| 5,594,248 A | 1/1997 | Tanaka | |
| 5,650,624 A | 7/1997 | Wong | |
| 5,721,430 A | 2/1998 | Wong | |
| 5,782,974 A | 7/1998 | Sorensen et al. | |
| 5,834,777 A | 11/1998 | Wong | |
| 5,932,877 A * | 8/1999 | Braig et al. | 250/343 |
| 5,962,854 A | 10/1999 | Endo | |
| 5,967,992 A | 10/1999 | Canfield | |
| 6,045,257 A | 4/2000 | Pompei et al. | |
| 6,122,042 A | 9/2000 | Wunderman et al. | |
| 6,348,650 B1 | 2/2002 | Endo et al. | |
| 6,370,950 B1 | 4/2002 | Lammerink | |
| 6,444,474 B1 | 9/2002 | Thomas | |
| 6,469,303 B1 | 10/2002 | Sun et al. | |
| 6,617,175 B1 | 9/2003 | Arno | |
| 6,649,994 B2 | 11/2003 | Parsons | |
| 6,694,800 B2 | 2/2004 | Weckstrom et al. | |
| 6,821,795 B2 | 11/2004 | Arno | |
| 6,828,172 B2 | 12/2004 | Chavan et al. | |
| 6,909,093 B2 | 6/2005 | Sato et al. | |
| 7,009,267 B2 | 3/2006 | Honboh | |
| 7,011,614 B2 | 3/2006 | Arno | |
| 7,033,542 B2 | 4/2006 | Archibald et al. | |
| 7,129,519 B2 | 10/2006 | Arno | |
| 7,172,918 B2 | 2/2007 | Arno | |
| 7,351,976 B2 | 4/2008 | Arno | |
| 2002/0049389 A1 | 4/2002 | Abreu | |
| 2002/0051132 A1 | 5/2002 | Ohno et al. | |
| 2002/0168289 A1 | 11/2002 | McVey | |
| 2004/0038442 A1 | 2/2004 | Kinsman | |
| 2005/0211555 A1 | 9/2005 | Archibald | |
| 2006/0219923 A1 | 10/2006 | Uchida et al. | |
| 2006/0263916 A1 | 11/2006 | Arno | |

OTHER PUBLICATIONS

IEEE, "The Authoritative Dictionary of IEEE Standard Terms, Seventh Edition", Jan. 2001, p. 1174 Publisher: The Institute of Electrical and Electronics Engineers, Inc.

Schilz, Jurgen, "Applications of thermoelectric infrared sensors (thermopiles): Gas detection by infrared absorption; NDIR", "Thermophysica Minima", Aug. 22, 2000, Publisher: PerkinElmer.

Thermometrics Global Business, "Application note of thermopile sensors (Rev.02)", 2000, pp. 1-9.

Wilks, Paul A., "The birth of infrared filtometry", "Spectroscopy Showcase—www.spectroscopyonline.com", Mar. 2002, pp. 14.

* cited by examiner

MONITORING SYSTEM COMPRISING INFRARED THERMOPILE DETECTOR

CROSS REFERENCE TO RELATED APPLICATIONS

This is a continuation of U.S. patent application Ser. No. 11/555,094 filed on Oct. 31, 2006, and subsequently issued as U.S. Pat. No. 7,351,976 on Apr. 1, 2008, which is a continuation of U.S. patent application Ser. No. 10/668,489 filed on Sep. 23, 2003 and subsequently issued as U.S. Pat. No. 7,129,519, which is a continuation-in-part of U.S. patent application Ser. No. 10/623,244 filed on Jul. 18, 2003 and subsequently issued as U.S. Pat. No. 7,011,614, which is a divisional of U.S. patent application Ser No. 10/140,848 filed on May 8, 2002 and subsequently issued as U.S. Pat. No. 6,617,175. Each of the foregoing patents and patent applications is hereby incorporated by reference as if set forth fully herein.

FIELD OF THE INVENTION

This invention relates to infrared thermopile monitoring systems for semiconductor process monitoring and control.

DESCRIPTION OF THE RELATED ART

Most infrared energy-absorbing molecules absorb infrared radiation at discrete energy levels, so that when a gas, liquid or solid composition is exposed to infrared (IR) radiation of a broad wavelength range, the infrared energy-absorbing component(s) of that composition will absorb a portion of the IR light at very specific wavelengths. This phenomenon enables infrared-based detection, by comparing energy spectra of various known compositions with and without specific IR-absorbing component(s), to obtain an absorption profile or pattern that can be used to detect the presence of specific IR-absorbing component(s) in an unknown composition. Additionally, the concentration of the IR-absorbing component(s) in the composition directly correlates to the amount of IR light that is absorbed by such component(s), and can be determined based thereon.

Conventional IR gas analyzers depend on grating techniques or prisms to break IR radiation into its individual wavelengths (see FIGS. 1A and 1B, showing split IR lights of wavelength $\lambda_1$ and $\lambda_2$). The IR radiation of individual wavelengths would then be introduced into a gas cell by means of a moveable slit aperture and the IR radiation of the selected wavelength passing through the gas cell would be detected. Such dispersive IR analyzers used electronic processing means to correlate the slit aperture position with the IR energy level and the signal from the detector, and produce energy versus absorbance relations.

The principal drawbacks of the above-described dispersive spectrometers are the loss of radiation intensity due to multiple reflection and refraction, the risk of total system failure due to misalignment of the movable parts, the cost and complexity of the spectrometer apparatus due to the number of optical components (e.g., mirrors, lens, and prism), and the space requirement for accommodating the numerous optical components used.

Fourier transform IR (FT-IR) spectrometers, like dispersive spectrometers, also use broad energy IR sources. The originally generated IR beam is split into two beams and an interference pattern is created by sending one of the two beams in and out-of-phase, using a movable mirror. A laser beam is used to monitor the location of the movable mirror at all times. After the dual beam is sent to a sample, a sensor component of the spectrometer device receives the convoluted infrared wave pattern together with the laser-positioning beam. That information is then sent to a computer and deconvoluted using a Fourier transform algorithm. The energy versus mirror displacement data is thereby converted into energy versus absorbance relationships. Such FT-IR spectrometers suffer from similar drawbacks as described hereinabove for the conventional dispersive spectrometers.

It is therefore an object of the present invention to provide an IR photometer system that minimizes the loss of radiation intensity during transmission of the IR radiation.

It is another object of the present invention to provide an IR photometer system that is simple and robust, which is less vulnerable to misalignment.

It is still another object of the present invention to provide a scrubber system for abating semiconductor process effluent, which is capable of analyzing composition of the incoming effluent and responsively modifying the operational mode accordingly.

Other objects and advantages of the invention will be more fully apparent from the ensuing disclosure and appended claims.

SUMMARY OF THE INVENTION

In one aspect, the present invention relates to a system for treatment of an effluent material, said system comprising: an inlet conduit arranged to receive the effluent material from an upstream processing unit; a sampling region for the effluent material in flow communication with the inlet conduit, the sampling region defining a radiation transmission path; an infrared radiation source constructed and arranged to emit infrared radiation into the sampling region; and a thermopile detector constructed and arranged to receive at least a portion of the infrared radiation following passage thereof through the sampling region, and arranged to responsively generate an output signal correlative of at least one of (i) effluent material composition and (ii) concentration of an abatable component of the effluent material within the sampling region; and a control element arranged to receive the output signal from the thermopile detector and arranged to adjust an effluent treatment media flow based on the received output signal to maintain effluent material and/or abatable component discharge below a predetermined level.

In another aspect, the present invention relates to a method of generating an output signal indicative of presence or concentration of a desired component of a material, said method comprising emitting infrared radiation generated by an infrared radiation source into a sampling region defining a radiation transmission path and a material flow path, receiving at least a portion of said emitted infrared radiation with a thermopile detector, generating the output signal from said thermopile detector indicative of the presence or concentration of the desired component of said material in the sampling region, wherein the method is further characterized by any of the following: (a) flowing a gas through at least one gas introduction element between the infrared radiation source and the thermopile detector; (b) transmitting the infrared radiation along a transmission path that comprises an inner surface characterized by a roughness in a range of from about 0.012 μm Ra to about 1.80 μm Ra; and (c) heating at least a portion of said radiation transmission path with a heating element that is distinct from the infrared radiation source.

In one embodiment, infrared (IR) radiation in a system according to the present invention is transmitted along a transmission path that is substantially linear, while both the infrared radiation source and the thermopile detector are aligned along the transmission path of said infrared radiation. The linear transmission path for the IR radiation minimizes reflection and refraction of such IR radiation and therefore significantly reduces loss of radiation intensity during transmission. Such linear transmission path is made available by the integration of the thermopile detector, which comprises one or more radiation filters for selectively transmitting the IR radiation of a specific wavelength, therefore eliminating the requirements for monochromating the IR radiation through splitting and grating that are essential to the conventional dispersive and FT-IR spectrometers.

The loss of IR radiation intensity can also be reduced, either independent from or in addition to the use of linear transmission path, by providing a transmission path with inner surface that is sufficient smooth and/or reflective, which minimizes absorption and dissipation of the IR radiation by such inner surface of the transmission path. Specifically, such inner surface of the transmission path is characterized by a roughness in a range of from about 0.012 µm Ra to about 1.80 µm Ra, preferably from about 0.10 µm Ra to about 0.80 µm Ra, and more preferably from about 0.10 µm Ra to about 0.20 µm Ra. Such inner surface may further be characterized by a reflectivity in a range of from about 70% to about 99%, preferably from about 92% to about 97%.

"Ra" as used herein refers to the average differences between peaks and valleys of a surface finish.

When the material is subjected to IR radiation in the sampling region is a process gas, such material may comprise particles or be susceptible to particle formation, resulting in deposition of particles around the IR radiation source or the thermopile detector, which may in turn significantly reduce the amount of IR radiation transmitted therethrough or completely block the transmission path.

Various embodiments of the present invention can be arranged and constructed to utilize a purge gas for purging the interfacial spaces between the sampling region containing the process gas and the IR radiation source as well as between the sampling region and the thermopile detector. Such purge gas can be passed through porous media into the interfacial spaces, to form a purge gas flow that moves any particle deposits away from the IR radiation source and the thermopile detector into the sampling region. Alternatively, particle deposit may be reduced by providing external thermal energy for heating at least a portion of the IR transmission path, so as to create a thermal gradient or heat flux that hinders the particle access to the internal surface of the transmission path.

A semiconductor process system according to one embodiment of the present invention may comprise a scrubber unit for abating a semiconductor process effluent from an upstream process unit, with a sampling region arranged near the inlet of such scrubber unit, so as to enable analysis of the effluent before its entry into such the scrubber unit, thereby enabling the scrubber unit to be responsively operated according the composition of the process gas.

Other aspects, features and embodiments of the invention will be more fully apparent from the ensuing disclosure and appended claims.

DETAILED DESCRIPTION OF THE INVENTION, AND PREFERRED EMBODIMENTS THEREOF

Figure 1A:
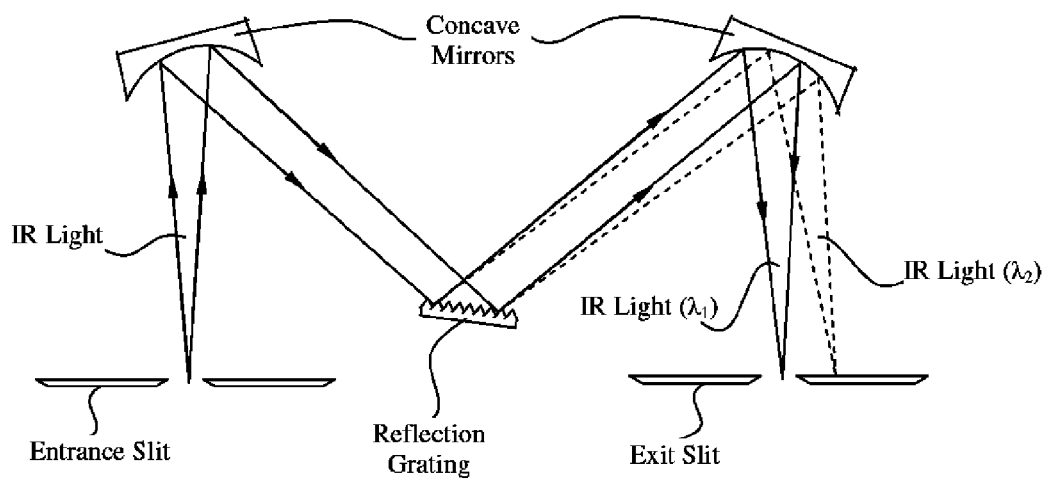
FIGS. 1A and 1B show conventional monochromator systems for splitting and grating IR radiation.

The present invention provides infrared thermopile detector systems useful for semiconductor process monitoring and control. U.S. patent application Ser. No. 10/140,848 filed on May 8, 2002 in the name of Jose I. Arno, and issued as U.S. Pat. No. 6,617,175 on Sep. 9, 2003, is incorporated herein by reference in its entirety for all purposes.

As used herein, the term "semiconductor process" is intended to be broadly construed to include any and all processing and unit operations involved in the manufacture of semiconductor products, as well as all operations involving treatment or processing of materials used in or produced by a semiconductor manufacturing facility, as well as all operations carried out in connection with the semiconductor manufacturing facility not involving active manufacturing (examples include conditioning of process equipment, purging of chemical delivery lines in preparation for operation, etch cleaning of process tool chambers, abatement of toxic or hazardous gases from effluents produced by the semiconductor manufacturing facility, etc.).

The thermopile-based infrared monitoring system of the invention comprises an infrared (IR) radiation source, a sampling region for exposing a material of interest (e.g., a process gas) to IR radiation, and a thermopile detector for analyzing the IR radiation as transmitted through the material of interest. The sampling region in the broad practice of the invention may comprise any suitable compartment, passageway or chamber, in which the material to be analyzed is subjected to passage of IR light therethrough for the purpose of using its IR absorbance-determined output to generate control signal(s) for process monitoring and control. The thermopile detector generates small voltages when exposed to IR light (or heat in the IR spectral regime). The output signal of the thermopile detector is proportional to the incident radiation on the detector.

Thermopile detectors employed in the preferred practice of the present invention may have a multiple array of elements in each detector unit. For instance, in a dual element detector, one of the thermopile detector elements is used as a reference, sensing IR light in a range in which substantially no absorption occurs (e.g., wavelength of 4.00±0.02 μm). The second thermopile detector element is coated with a filter that senses IR energy in the spectral range of interest (such spectral range depending on the particular material to be monitored). Comparison of the differences in the voltages generated by the reference thermopile detector element and those generated by the thermopile detector active element(s) provides a concentration measurement. Detectors with up to 4 thermopile detector element arrays are commercially available. For example, in a 4-element detector unit, one detector element is employed as a reference and the remaining 3 detector elements are utilized for measurements in different spectral regions.

While the ensuing disclosure is directed to a process gas as the material being subjected to IR radiation, it will be recognized that the invention is applicable to a wide variety of materials, e.g., solids, fluids (liquids and gases), multiphase materials, multicomponent materials, supercritical media, etc.

The total loss of the IR radiation intensity (referred to herein as $L_{Total}$) is determined by both the loss of IR radiation intensity caused by transmission thereof (i.e., absorption by the transmission path and the optical components, referred to herein as $L_{Path}$) and the loss of IR radiation intensity due to absorption by the IR-absorbing material of interest (referred to herein as $L_{Material}$), according to the following equations:

$$L_{Total} = L_{Path} + L_{Material}$$

The thermopile IR detector has a minimum requirement for the IR radiation intensity, in order to effectively detect such IR radiation. Therefore, when the intensity of the IR radiation generated by the IR source remains constant, the $L_{Total}$ has to be maintained at a level that is equal to or smaller than a maximum limit $L_0$ in order to enable detection of the IR radiation by the thermopile IR detector. On the other hand, since the concentration of the IR-absorbing material of interest directly correlates to and is determined by $L_{Material}$, maximization of $L_{Material}$ will maximize the signal strength of the measurement, which is especially important for detection and analysis of low concentration IR-absorbing materials.

Figure 1B:
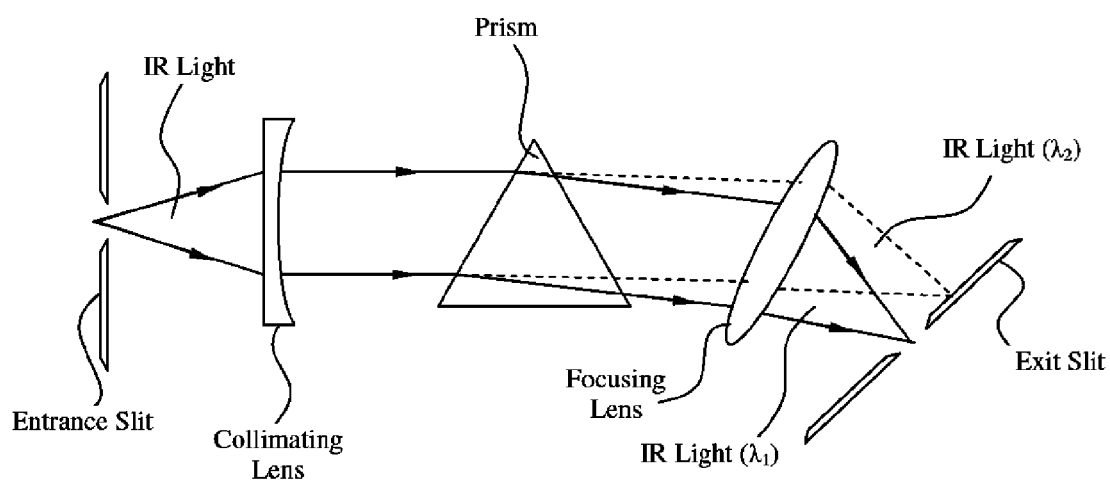

The present invention achieves the goal of maximizing $L_{Material}$ while maintaining $L_{Total}$ at or below a maximum limit $L_0$, by reducing or minimizing $L_{Path}$, according to the following methods:

When the IR radiation is transmitted through a substantially linear transmission path from the IR source to the thermopile detector, with minimum amount of reflection and refraction therebetween, the loss of radiation intensity is effectively reduced in comparison to that of a non-linear transmission path that requires multiple reflections and refractions of the IR radiation, as shown in FIGS. 1A and 1B.

Figure 2:
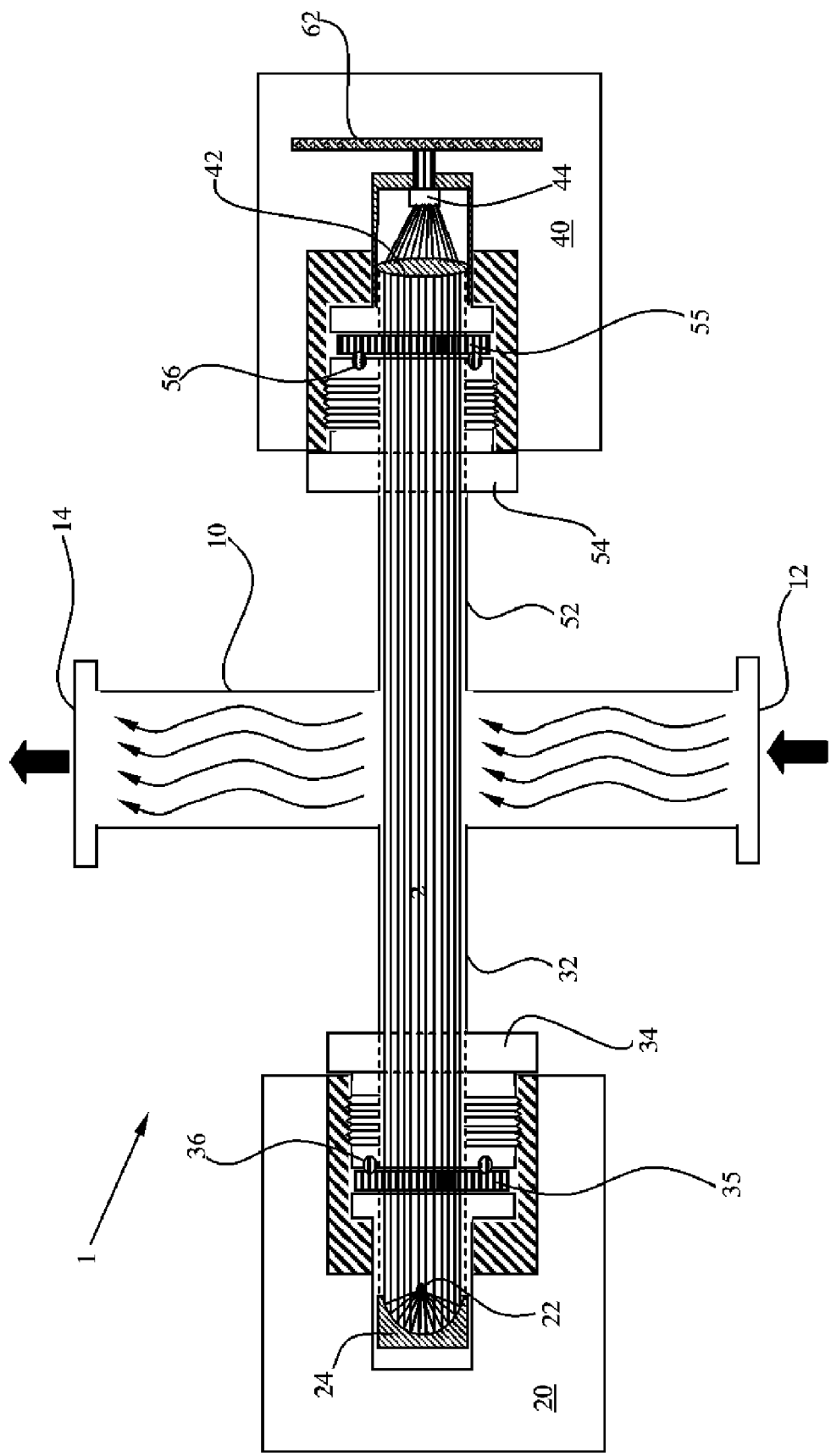
FIG. 2 is a schematic view of a semiconductor process system comprising a linear transmission path for IR radiation, according to one embodiment of the present invention.

Therefore, the present invention constructs and arranges the IR radiation source, the sampling region, and the thermopile detector to provide a substantially linear transmission path for the IR light, as shown in FIG. 2.

Specifically, the system 1 comprises a sampling region 10, preferably a gas sampling region having a gas inlet 12 and a gas outlet 14 and constitutes a part of a flow circuitry for flow of a process gas therethrough.

The IR radiation source 20 is positioned at one side of such gas sampling region 10. Specifically, the IR radiation source 20 comprises an IR emitter 22 and a parabolic mirror 24, for providing a parallel beam of IR light 2, which is transmitted along a substantially linear transmission path through the gas sampling region 10.

The thermopile detector 40 is positioned at the other side of such gas sampling region 10 for receiving and analyzing the transmitted IR light beam. The thermopile detector 40 comprises an IR detecting element 44 having one or more IR radiation band pass filters for selectively transmitting a portion of the IR radiation of a narrow wavelength range that encompasses the absorption wavelength that is characteristic to the IR-absorbing component(s) of interest in the process gas, so that the decrease in output signal generated by such thermopile is directly related to the amount of infrared absorption by the corresponding component(s) of interest. Preferably but not necessarily, the IR light beam is focused by a focusing lens 42 before entering the IR detecting element 44. The thermopile detector unit as mentioned may further include a multiplicity of absorber areas, including reference (unfiltered) absorber and gas-filtered absorber regions, with the latter filters being gas-specific for sensing of the semiconductor gases or gas components of interest (e.g., arsine, phosphine, germane, stibine, distibine, silane, substituted silanes, chlorine, bromine, organometallic precursor vapor, etc.).

The gas sampling region 10 is separated from the IR radiation source 20 and the thermopile detector 40 by interfacial spaces 32 and 52, which form parts of the IR transmission path. Preferably, the interfacial space 32 is connected to the IR radiation source 20 in a sealed manner, which comprises a weld connector 34 that is detachably and sealingly connected to the IR radiation source by a spacer 35 and O-rings 36. Similarly, the interfacial space 52 is connected to the thermopile detector 40 in a sealed manner, which comprises a weld connector 54 that is detachably and sealingly connected to the IR radiation source by a spacer 55 and O-rings 56. Such weld connector 34 and 54 both comprise IR transparent materials and therefore form a portion of the IR transmission path.

The linear transmission path of the IR radiation reduces unnecessary loss of radiation intensity. In addition, connection between the IR source, the gas sampling region, and the thermopile detector is simple and robust, providing a sufficient small footprint and efficient resistance against misalignment.

Further, an integrated circuit board 62 may be positioned behind the thermopile detector 40, for immediately receiving output signals from the thermopile detector 40, so as to further reduce the footprint and minimize signal loss due to remote connections.

In one illustrative embodiment of the invention, the thermopile detector system is utilized as an abatement tool controller for an abatement unit for treating process effluent produced in a semiconductor manufacturing operation, or other industrial process. For such purpose, the thermopile detector system advantageously is installed at the inlet of the abatement unit, where the abatement apparatus receives the effluent to be treated. In such service, the thermopile detector system is used to sense whether or not an upstream tool that generates the effluent in active on-stream operation, is in an active operating mode, or alternatively whether or not the upstream tool is in a non-effluent-producing state, e.g., undergoing purging or cleaning. The thermopile detector unit, by way of specific example, is usefully employed as an abatement tool controller for an effluent scrubber, such as a wet/dry scrubber or a thermal scrubber, whereby the presence of the thermopile detector system transforms the scrubber into a "smart" scrubber and enhances the efficiency of the scrubber, allowing conservation of resources (lower consumables) to be achieved.

Figure 3:
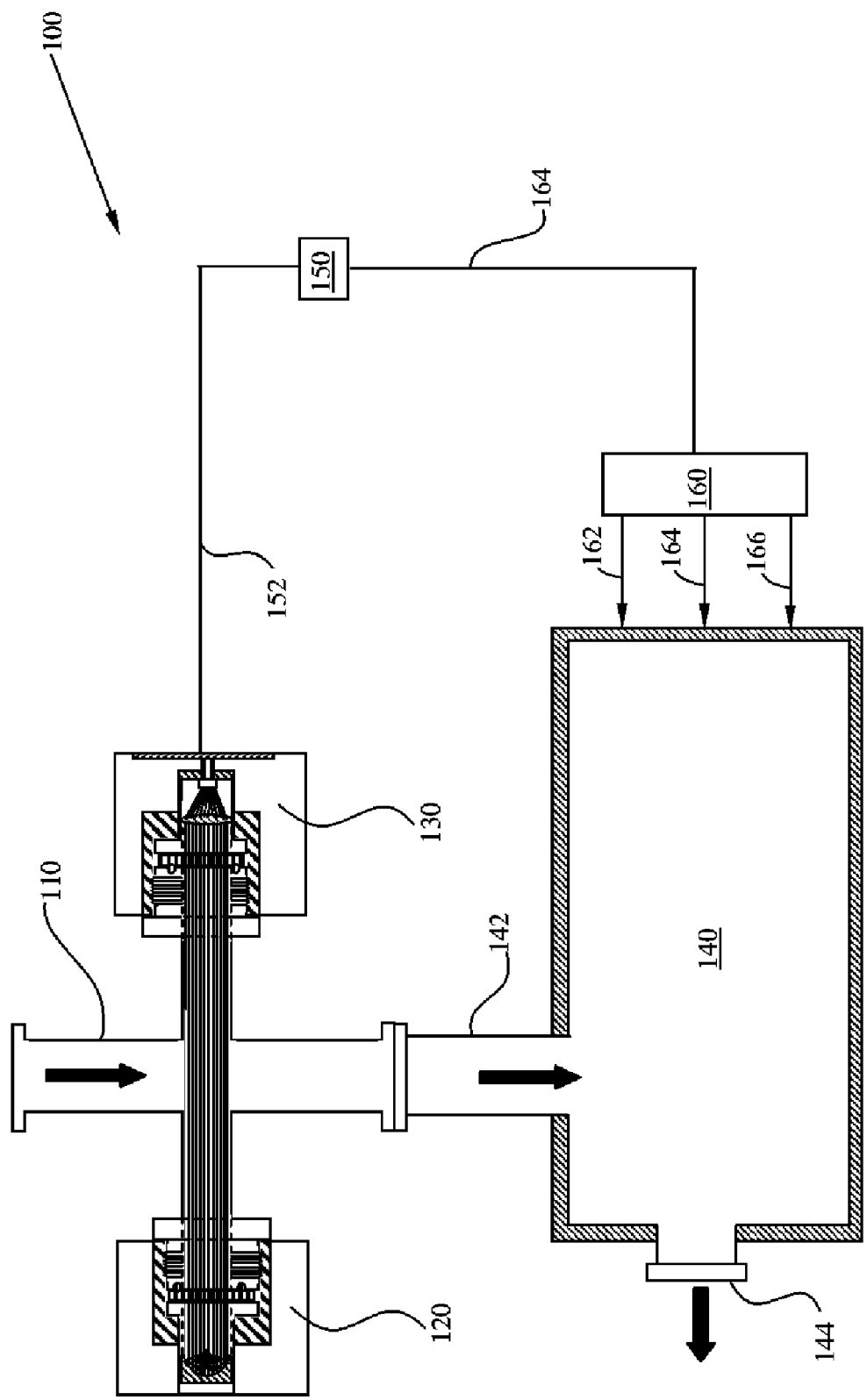
FIG. 3 is a schematic view of a semiconductor process system comprising a scrubber unit having an IR radiation source and a thermopile detector constructed and arranged for analyzing an incoming process effluent near the inlet of such scrubber unit, according to one embodiment of the present invention.

FIG. 3 shows a semiconductor process system 100 comprising a scrubber unit 140 having a gas inlet 142 and a gas outlet 144. An IR source 120 and a thermopile detector 130 are provided at both sides of a gas sampling region 110 near the gas inlet 142 of such scrubber unit 140, for analyzing the composition of the effluent flowed into the scrubber. The output signal generated by the thermopile detector 130 is forwarded through transmission line 152 to a microcontroller 150. The microcontroller 150 is connected to the scrubbing medium sources 160 and responsively adjusts the amount of scrubbing media (preferably fuel, water, and chemical additives) 162, 164, and 166 input according to the composition of the effluent as measured.

Various abatable components in the effluent, including but not limited to, tetraethyloxysilane, silane, silicon tetrafluoride, silicon-containing organic compounds, boranes, arsenic hydride, phosphine, hydrogen fluoride, fluorine, tungsten hexafluoride, hydrogen chloride, chlorine, titanium tetrachloride, perfluorocarbons, nitrous oxide, ammonium, hydrogen, oxygen, argon, and helium, may be analyzed by the thermopile detector system of the present invention. Additional sensors, such as temperature sensors, flow sensors, pressure transducers, ultraviolet spectrometers, mass spectrometers, and electrochemical sensors, may be provided for further measuring the flow rate, gas composition and concentration, pressure, and temperature of the effluent, so as to allow corresponding adjustment of the operational mode of the scrubber unit.

Figure 4:
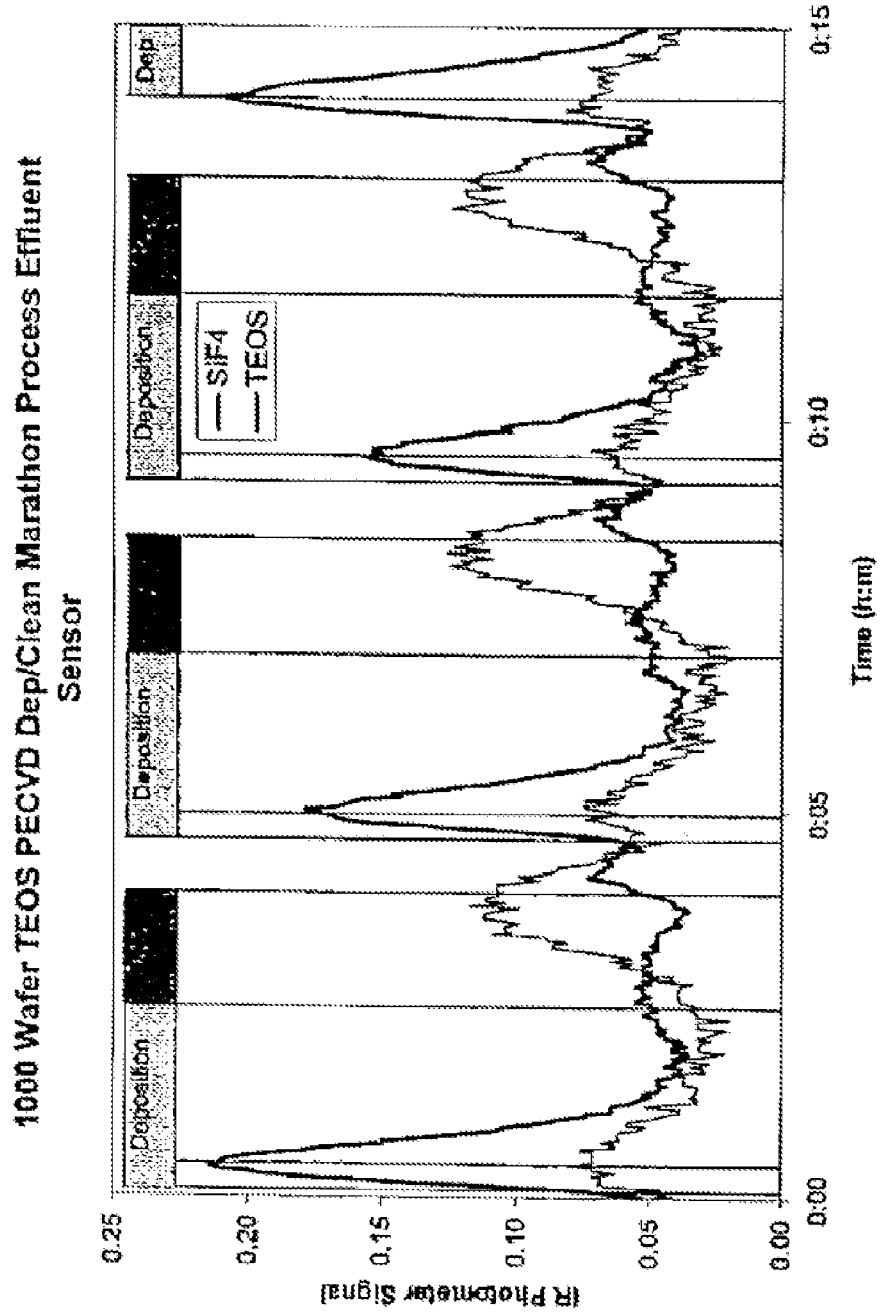
FIG. 4 is a time-concentration plot of tetraethyloxysilane (TEOS) and silicon tetrafluoride ($SiF_4$) as measured for the process effluent from an upstream plasma enhanced chemical vapor deposition chamber that is operated according to alternative deposition and cleaning cycles.

The IR thermopile detector system of the present invention may be used to analyze the effluent gas species emitted from a plasma enhanced chemical vapor deposition (PECVD) chamber, in which $SiO_2$ films are deposited using tetraethyloxysilane (TEOS) and which performs chamber cleaning by using $SiF_4$ after each deposition cycle. Therefore, during the deposition cycles, the IR detector system measures the real-time concentration of TEOS in the deposition effluent. During alternating cleaning cycles, the IR detector system measures the $SiF_4$ concentration. Measurements obtained by the IR detector system during the alternating deposition/cleaning cycles are provided in FIG. 4. The information collected by the IR photometer can be used to adjust the settings of the downstream scrubber unit for abatement of TEOS and $SiF_4$.

For further reduce the IR radiation loss ($L_{Path}$) during the transmission, a transmission path with a smooth, reflective inner face is provided, which minimize the absorption and dissipation of IR radiation by the surface of such transmission path.

When such smooth, reflective transmission path is provided, longer path length can be provided for maximizing the absorption of IR radiation by the IR-absorbing components of interest (i.e., $L_{Gas}$), which is especially important for effectively measuring low concentration IR-absorbing components.

Preferably, such inner surface of the transmission path is characterized by a roughness in a range of from about 0.012 μm Ra to about 1.80 μm Ra, more preferably from about 0.10 μm Ra to about 0.80 μm Ra, and most preferably from about 0.10 μm Ra to about 0.20 μm Ra. Such inner surface may further be characterized by a reflectivity in a range of from about 70% to about 99%, preferably from about 92% to about 97%. Such smooth, reflective inner surface may be provided by electropolishing or super polishing techniques.

Figure 5:
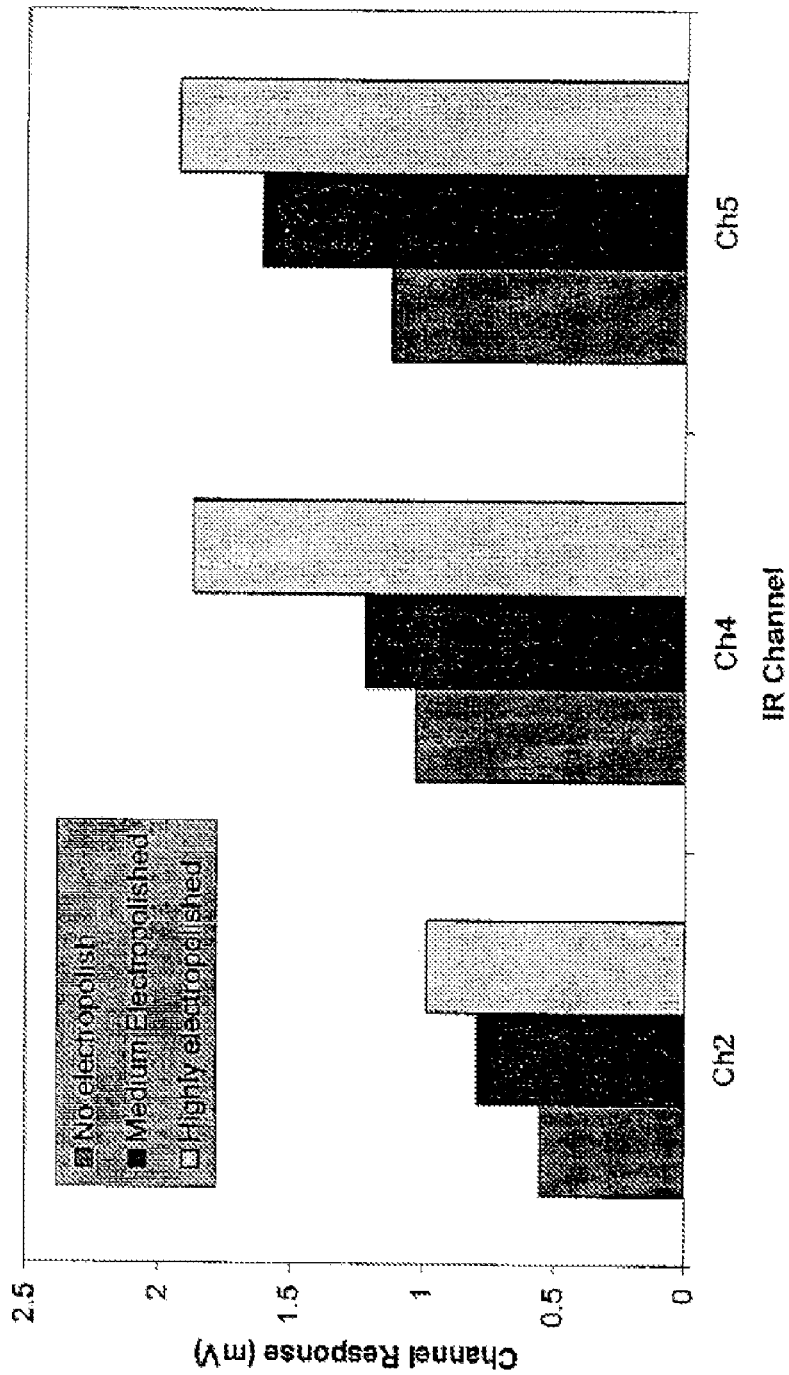
FIG. 5 is a graph showing the IR signal responses measured for a first transmission path having non-electropolished inner surface, a second transmission path having moderately electropolished inner surface, and a third transmission path having highly electropolished inner surface, at various IR wavelengths.

FIG. 5 shows the IR signal responses measured for a first transmission path having non-electropolished inner surface, a second transmission path having moderately electropolished inner surface, and a third transmission path having highly electropolished inner surface, at various IR wavelengths (Channel 2=3.88 μm, Channel 4=4.65 μm, and Channel 5=4.2 μm). The path length for each transmission path is the same, and the same IR source and thermopile detector are used. The measurement results indicate that the highly polished transmission path provides much stronger signal strength than that of the moderately polished and non-polished transmission paths.

Process gas that contains particles or is susceptible to particles formation may form particle deposits along the transmission path of the IR radiation, which will absorb the IR radiation and significantly reduces the radiation intensity of the IR radiation transmitted.

The present invention therefore provides a purge gas near the interfacial spaces between the gas sampling region and the IR source as well as between the gas sampling region and the thermopile detector. The purge gas flow provides a sufficient force to remove the particle deposits away from the IR source and the thermopile detector, so as to prevent such particles from interfering with the detection process.

Figure 6:
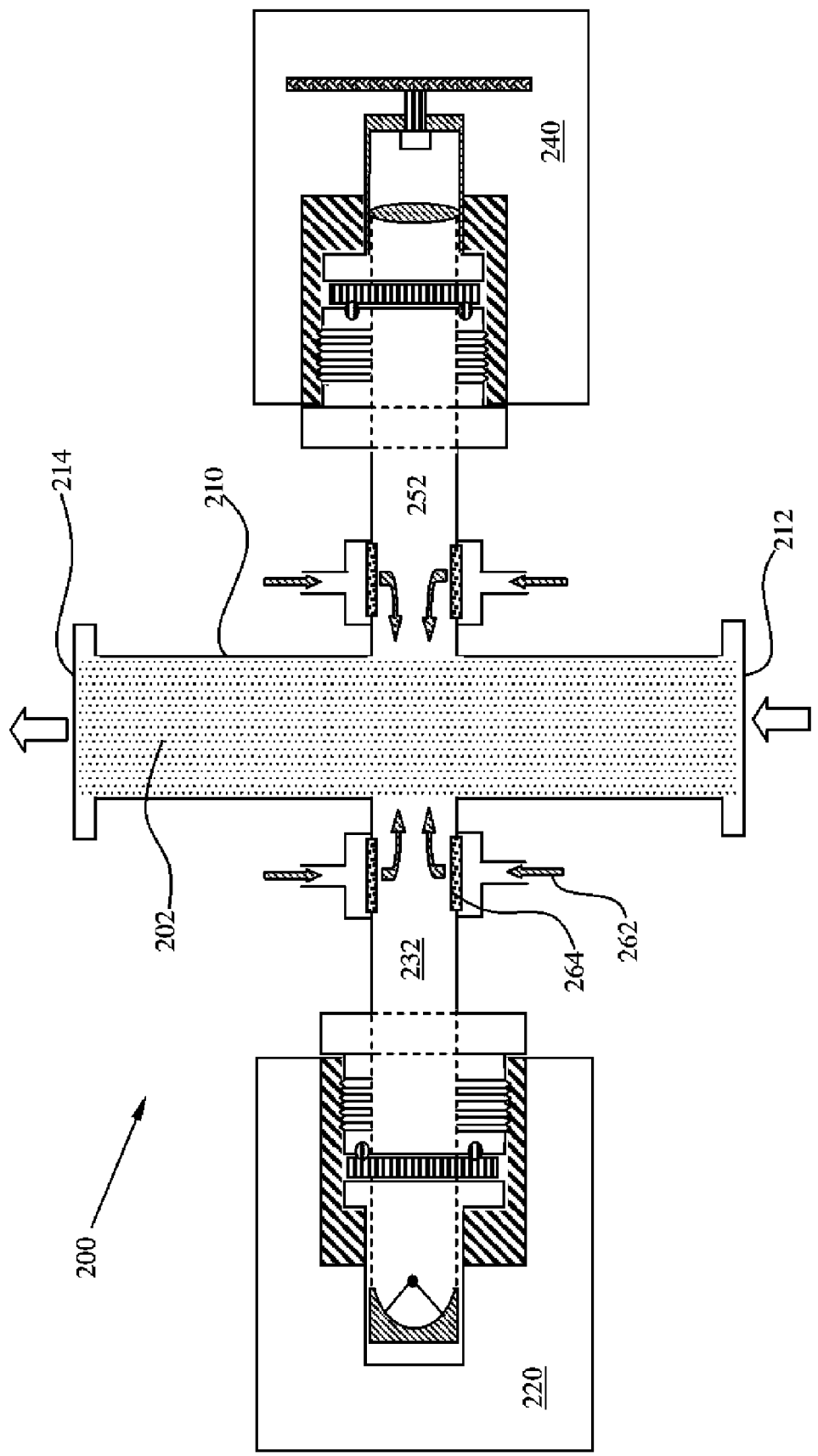
FIGS. 6 and 7 are perspective views of semiconductor process systems comprising purge gas inlets for introducing a purge gas to remove particles from the interfacial spaces between the sampling region and the IR source as well as between the sampling region and the thermopile detector.

FIG. 6 shows a gas sampling region 210 having an inlet 212 and an outlet 214 for flowing a particle-containing process gas 202 therethrough. An IR source 220 is positioned at one side of such gas sampling region 210 and is isolated therefrom by an interfacial space 232, while a thermopile detector 240 is positioned at the other side of such gas sampling region 210 and is isolated therefrom by an interfacial space 252. A purge gas 262 is introduced into such interfacial spaces 232 and 252 from a purge gas source (not shown), preferably through a porous media 264, for forming a uniform flow of purge gas that moves away from the IR source 220 and the thermopile detector 240 toward the gas sampling region 210. Such flow of purge gas further generates vacuum at the dead-end spaces near the IR source 220 and the thermopile detector 240, so as to force the particle deposits out of such dead-end spaces and discharge same into the process gas flow in the gas sampling region 210.

The purge gas may be introduced into the interfacial spaces 232 and 252 along a direction that is substantially parallel to the process gas flow, as shown in FIG. 6, which then flows through such interfacial spaces into the gas sampling region 210 in a direction that is substantially perpendicular to the process gas flow.

Figure 7:
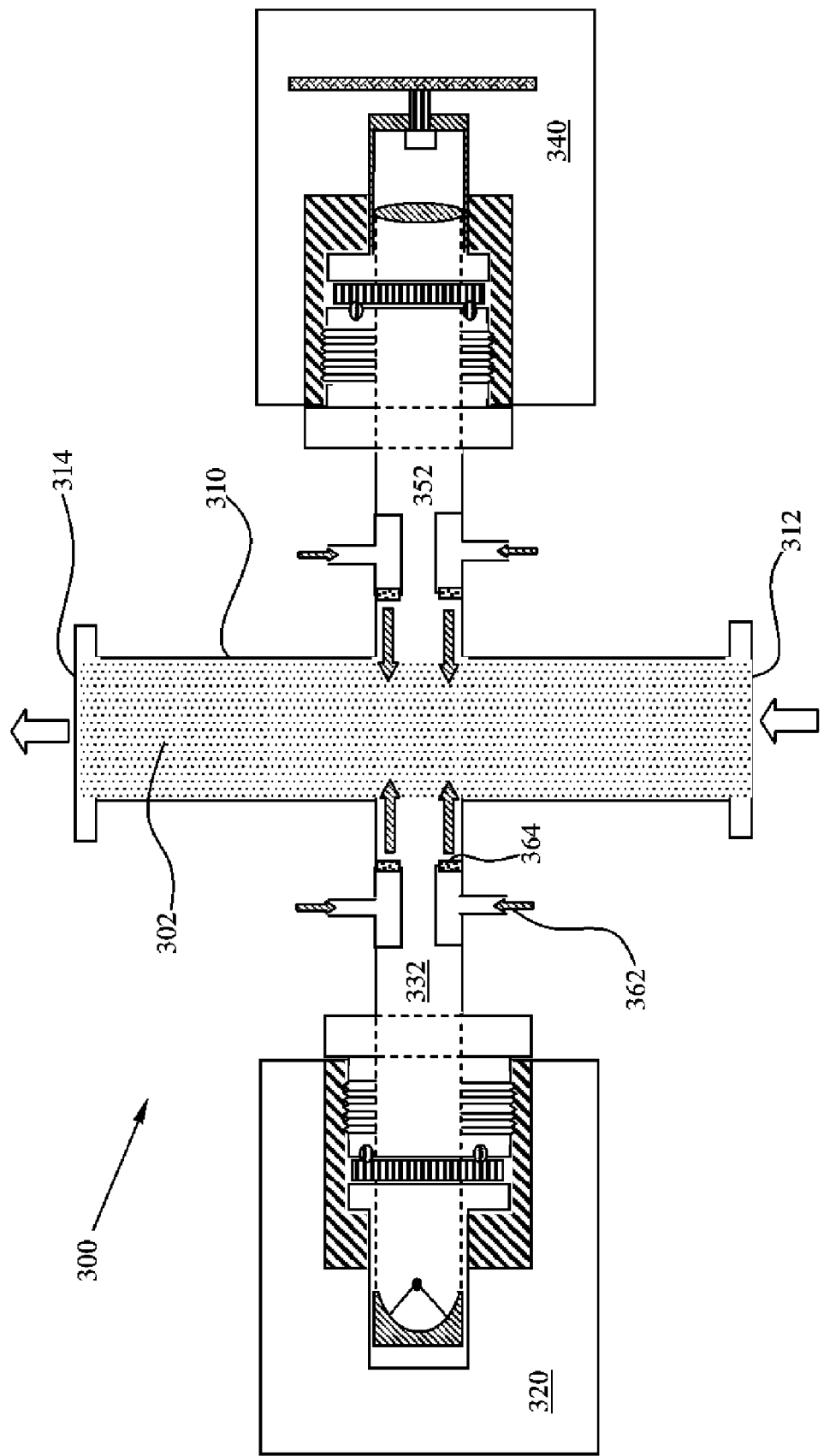

FIG. 7 shows an alternative embodiment of the present invention, in which the purge gas is introduced into the interfacial spaces 332 and 352 in a direction that is substantially perpendicular to the process gas flow and flows through such interfacial spaces along the same direction into to the gas sampling region 210.

Figure 8:
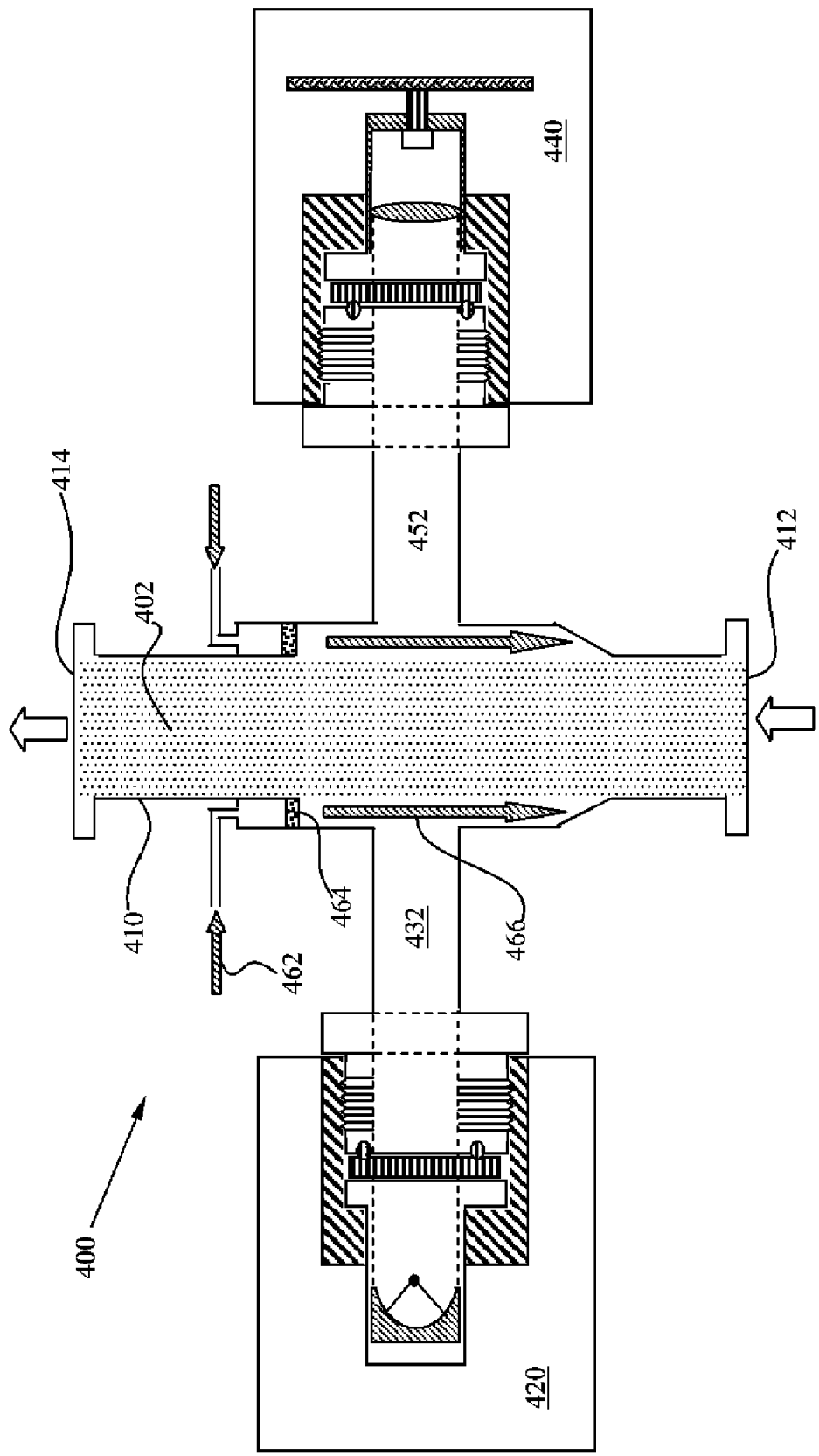
FIG. 8 is a perspective view of semiconductor process system comprising purge gas inlets for forming a sheath of purge gas around the particle-containing process effluent in the sampling region.

Further, the purge gas may be provided to form a gas sheath surrounding the process gas flow, so as to prevent particles from escaping from the gas sampling region. Specifically, FIG. 8 shows a purge gas 362 that forms an annular sheath 466 around the particle-containing process gas flow. Such purge gas is flowed in a direction that is confluent with the process gas flow and is therefore discharged of the gas sampling region 410 together with the process gas.

Alternatively, external heating devices can be provided for heating at least a portion of the IR transmission path (including the IR transmission windows), so as to generate a thermal gradient or heat flux, which functions to prevent the particles from accessing and depositing on the internal surface of the IR transmission path.

Although the invention has been variously disclosed herein with reference to illustrative embodiments and features, it will be appreciated that the embodiments and features described hereinabove are not intended to limit the invention, and that other variations, modifications and other embodiments will suggest themselves to those of ordinary skill in the art. The invention therefore is to be broadly construed, consistent with the claims hereafter set forth.

What is claimed is:

1. A system for treatment of an effluent material, said system comprising:
   an inlet conduit arranged to receive the effluent material from an upstream processing unit;
   a sampling region for the effluent material in flow communication with the inlet conduit, the sampling region defining a radiation transmission path;
   an infrared radiation source constructed and arranged to emit infrared radiation into the sampling region; and
   a thermopile detector constructed and arranged to receive at least a portion of the infrared radiation following passage thereof through the sampling region, and arranged to responsively generate an output signal correlative of at least one of (i) effluent material composition and (ii) concentration of an abatable component of the effluent material within the sampling region; and
   a control element arranged to receive the output signal from the thermopile detector and arranged to control an effluent abatement apparatus, based on the received output signal to maintain effluent material and/or abatable component discharge below a predetermined level.

2. The system of claim 1, further comprising any of the following:
   (a) a heating element distinct from said infrared radiation source is adapted to heat at least a portion of the transmission path;
   (b) said transmission path comprises an inner surface characterized by a roughness in a range of from about 0.012 µm Ra to about 1.80 µm Ra; and
   (c) at least one gas introduction element is arranged to introduce a gas between the infrared radiation source and the thermopile detector.

3. The system of claim 2, comprising a heating element distinct from said infrared radiation source is adapted to heat at least a portion of the transmission path.

4. The system of claim 2, wherein the transmission path comprises an inner surface characterized by a roughness in a range of from about 0.012 µm Ra to about 1.80 µm Ra.

5. The system of claim 2, comprising at least one gas introduction element arranged to introduce a gas between said infrared radiation source and said thermopile detector.

6. The system of claim 5, wherein the effluent material comprises particles subject to being deposited in or on any of the infrared source, the sampling region, and the thermopile detector, and said at least one gas introduction element is adapted to reduce formation of or remove particles in or on any of the infrared source, the sampling region, and the thermopile detector.

7. The system of claim 5, wherein said at least one gas introduction element is adapted to introduce the gas along a direction that is substantially perpendicular to the effluent material flow.

8. The system of claim 5, wherein said at least one gas introduction element is adapted to introduce the gas along a direction that is substantially parallel to the effluent material flow.

9. The system of claim 5, wherein:
   said at least one gas introduction element is adapted to generate one or more sheaths of gas that encompass a flow of the effluent material through the sampling region;
   said at least one gas introduction element comprises at least one porous medium through which said gas flows;
   said inner surface has a roughness in a range of from 0.10 µm Ra to 0.80 µm Ra and a reflectivity in a range of from 70% to 99%;
   said radiation transmission path is substantially linear; and
   said infrared radiation source and said thermopile detector are aligned along opposing ends of said radiation transmission path.

10. The system of claim 1, wherein the control element comprises an integrated circuit board that is arranged in immediate signal receiving relationship with said thermopile detector for minimizing signal loss during signal transmission, wherein said integrated circuit board is positioned adjacent to said thermopile detector.

11. The system of claim 1, wherein the thermopile detector is constructed and arranged to responsively generate an output signal correlative of effluent material composition.

12. The system of claim 1, wherein the thermopile detector is constructed and arranged to responsively generate an output signal correlative of a concentration of the abatable component.

13. The system of claim 1, wherein at least one infrared radiation filter element is optically coupled between the infrared radiation source and the thermopile detector.

14. The system of claim 13, wherein the at least one infrared radiation filter element is coupled to the thermopile detector.

15. The system of claim 13, wherein the at least one infrared radiation filter element is adapted to allow transmission or passage of a desired spectral portion of the infrared radiation, said portion being characterized by a predetermined wavelength range.

16. The system of claim 15, wherein said desired spectral portion of said infrared radiation encompasses an absorption wavelength that is characteristic to the concentration of the abatable component.

17. The system of claim 15, wherein said desired spectral portion of said infrared radiation encompasses an absorption wavelength that is characteristic to the effluent material composition.

18. The system of claim 15, wherein said desired spectral portion of said infrared radiation encompasses a wavelength substantially unabsorbed.

19. The system of claim 1, wherein the upstream processing unit comprises a chemical vapor deposition chamber.

20. A method for treatment of an effluent material from an upstream processing unit with an effluent abatement apparatus, said method comprising:
   providing a system for treatment of an effluent material, as claimed in claim 1;
   arranging the inlet conduit to receive the effluent material from the upstream processing unit;
   operating said system to generate the output signal correlative of at least one of (i) material effluent composition and (ii) concentration of an abatable component of the effluent material within the sampling region; and
   controlling the effluent abatement apparatus, with the control element receiving the output signal from the thermopile detector, based on the received output signal, to maintain effluent material and/or abatable component discharge below a predetermined level.

* * * * *